(12) United States Patent
Gabriele et al.

(10) Patent No.: US 10,918,724 B2
(45) Date of Patent: Feb. 16, 2021

(54) DERMOCOSMETIC COMPOSITIONS INCLUDING GLYCEROL-SEBACATE

(71) Applicant: THE SECANT GROUP, LLC, Telford, PA (US)

(72) Inventors: Peter D. Gabriele, Frisco, TX (US); Jeremy J. Harris, Doylestown, PA (US); Carissa Smoot, Harleysville, PA (US); Charles Brendan Nicholson, Coopersburg, PA (US); Stephanie Reed, Conshohocken, PA (US); Ryan R. Smalley, Lansdale, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 92 days.

(21) Appl. No.: 16/281,516

(22) Filed: Feb. 21, 2019

(65) Prior Publication Data
US 2019/0255180 A1     Aug. 22, 2019

Related U.S. Application Data

(60) Provisional application No. 62/633,380, filed on Feb. 21, 2018.

(51) Int. Cl.

| | |
|---|---|
| *A61K 9/70* | (2006.01) |
| *A61K 47/34* | (2017.01) |
| *A61P 17/02* | (2006.01) |
| *A61K 45/06* | (2006.01) |
| *A61Q 19/00* | (2006.01) |
| *A61K 8/37* | (2006.01) |
| *A61K 8/85* | (2006.01) |
| *A61L 27/34* | (2006.01) |
| *A61L 27/54* | (2006.01) |
| *A61Q 19/08* | (2006.01) |

(52) U.S. Cl.
CPC ............. *A61K 47/34* (2013.01); *A61K 8/375* (2013.01); *A61K 8/85* (2013.01); *A61K 9/7023* (2013.01); *A61K 45/06* (2013.01); *A61P 17/02* (2018.01); *A61Q 19/00* (2013.01); *A61L 27/34* (2013.01); *A61L 27/54* (2013.01); *A61L 2430/20* (2013.01); *A61Q 19/08* (2013.01)

(58) Field of Classification Search
None
See application file for complete search history.

(56) References Cited

U.S. PATENT DOCUMENTS

| | | |
|---|---|---|
| 7,332,152 B2 | 2/2008 | Sanzgiri et al. |
| 9,359,472 B2 | 6/2016 | Nicholson et al. |
| 2006/0018858 A1 | 1/2006 | Chen et al. |
| 2011/0236974 A1 | 9/2011 | Ogle et al. |
| 2016/0046832 A1 | 2/2016 | Wroblesky et al. |
| 2016/0128944 A1 | 5/2016 | Chawrai et al. |
| 2017/0246316 A1 | 8/2017 | Wroblesky et al. |
| 2017/0290950 A1 | 10/2017 | Wagner et al. |
| 2018/0050128 A1* | 2/2018 | Gabriele ............... C08L 31/06 |
| 2018/0280912 A1 | 10/2018 | Lu et al. |

FOREIGN PATENT DOCUMENTS

| | | |
|---|---|---|
| WO | 2014066724 A1 | 5/2014 |
| WO | 2014100718 A1 | 6/2014 |
| WO | 2016057662 A1 | 4/2016 |
| WO | 2017147457 A2 | 8/2017 |

OTHER PUBLICATIONS

Rai et al., "Synthesis, properties and biomedical applications of poly(glycerol sebacate) (PGS): A review", Progress in Polymer Science, vol. 37, pp. 1051-1078 (2012).

* cited by examiner

*Primary Examiner* — Susan T Tran
(74) *Attorney, Agent, or Firm* — McNees Wallace & Nurick LLC

(57) ABSTRACT

A method of forming a skin care product includes combining at least one additive including at least one active ingredient with at least one glycerol-sebacate component having repeating units of (glycerol sebacate), water, a co-solvent, and at least one of an emulsifier, a surfactant, and a bodying agent to form the skin care product. A dermocosmetic composition includes at least one additive including at least one active ingredient and at least one glycerol-sebacate component having repeating units of (glycerol sebacate). A method of skin care includes applying a dermocosmetic composition to a skin surface.

7 Claims, 7 Drawing Sheets

DERMOCOSMETIC COMPOSITIONS INCLUDING GLYCEROL-SEBACATE

CROSS-REFERENCE TO RELATED APPLICATIONS

This application claims priority to and the benefit of U.S. Provisional Application No. 62/633,380 filed Feb. 21, 2018, which is hereby incorporated by reference in its entirety.

FIELD OF THE INVENTION

This application is directed to dermocosmetic compositions. More particularly, the present application is directed to dermocosmetic compositions including glycerol-sebacate.

BACKGROUND OF THE INVENTION

In many cases, skin is a first line of defense for the human immune system and is the largest single and variable organ of the human body. Thus, skin health is an important first line of defense to maintaining good general health.

Skin condition is associated with a host of effects from disease, therapeutic treatments, such as chemotherapy, trauma, toxic contact or bites, burns, abrasion, compression, vascular conditions, infection, chronic diseases, and necrosis. Skin conditions considered for treatment by dermocosmetic compositions or care may include, but are not limited to, acne, photo-aging, natural aging processes, chronic disease comorbid conditions such as, for example, diabetes, couperose, dehydration, rosacea, inflammation, immune-inflammation, auto-immune disorders, irritation, allergic reactions, and environmental exposure. Additionally, immunoinflammatory conditions of the skin and/or gastrointestinal tract for treatment may include, but are not limited to, psoriasis, scleroderma, Crohn's disease, ulcerative colitis, psoriatic arthritis, and atopic dermatitis.

Dermocosmetic compositions are skin care compositions recommended by health care professionals, such as, for example, by a doctor, a dermatologist, a pediatrician, an aesthetic physician, or a pharmacist, for specific skincare needs, because their ingredients are safe and effective with a marginal medicinal effect. As of 2018, the annual dermocosmetic market is about $3 billion (US) and expected to continue to grow based on increases in the aging population, diabetes, skin cancer, environmental damage, poor nutrition, and men's care.

Conventional dermocosmetic compositions include at least one active ingredient, where the active ingredient has an effectiveness against a specific condition documented through rigorous laboratory testing. These dermocosmetic compositions are typically distributed through traditional healthcare channels, such as pharmacies, over-the-counter (OTC) pharmaceutical drugstores, clinics, medical treatment spas, and dermatologists' offices.

BRIEF DESCRIPTION OF THE INVENTION

It would be desirable to provide a dermocosmetic composition including a carrier or controlled release vehicle that itself is also beneficial to the skin.

In an embodiment, a method of skin care includes applying a dermocosmetic composition to a skin surface. The dermocosmetic composition includes at least one additive comprising at least one active ingredient and at least one glycerol-sebacate component having repeating units of (glycerol sebacate).

In another embodiment, a dermocosmetic composition includes at least one additive including at least one active ingredient and at least one glycerol-sebacate component having repeating units of (glycerol sebacate).

In yet another embodiment, a method of forming a skin care product includes combining at least one additive including at least one active ingredient with at least one glycerol-sebacate component having repeating units of (glycerol sebacate), water, a co-solvent, and at least one of an emulsifier, a surfactant, and a bodying agent to form the skin care product.

In another embodiment, a method of skin care includes providing a dermocosmetic composition including at least one glycerol-sebacate component having repeating units of (glycerol sebacate). The dermocosmetic composition has an effective amount of the at least one glycerol-sebacate component to alter an expression of at least one gene in skin after application of the dermocosmetic composition to the skin surface. The method also includes applying the dermocosmetic composition to a surface of the skin such that the expression of the at least one gene in the skin is altered by the at least one glycerol-sebacate component.

Various features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
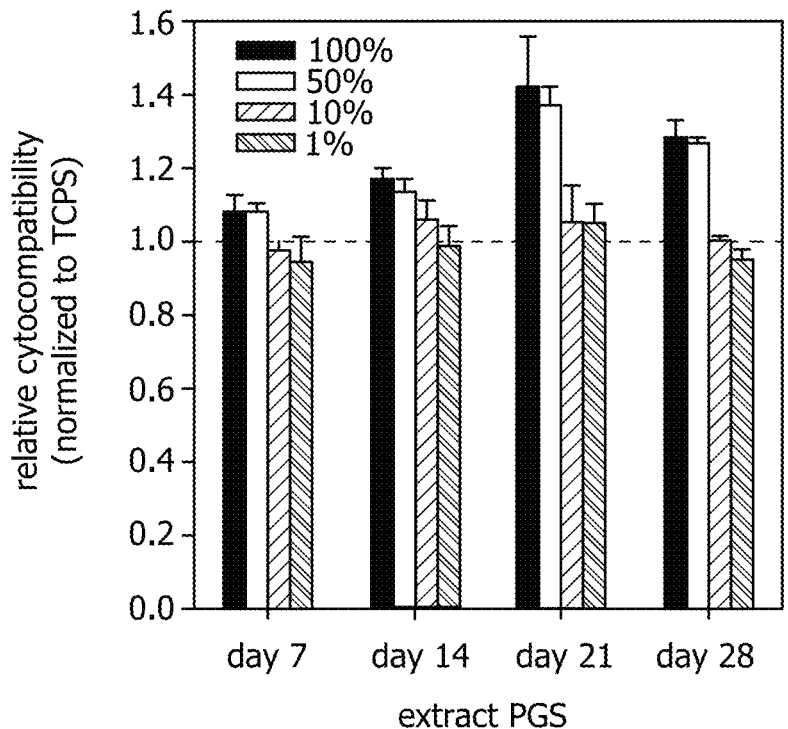
FIG. 1 shows the effect of poly(glycerol sebacate) (PGS) degradation on human Schwann cell proliferation.

Treatment of skin conditions and maintenance of skin health involve biological mechanisms similar to those found in regenerative medicine and tissue engineering.

In exemplary embodiments, a dermocosmetic composition includes at least one additive including at least one active ingredient and at least one glycerol-sebacate component having repeating units of (glycerol sebacate). Depending on the application of the dermocosmetic composition, the dermocosmetic composition may further include one or more additives in addition to the at least one active ingredient. Additional additives may include, but are not limited to, water, a co-solvent, an emulsifier, a surfactant, a bodying agent, and a filler.

As used herein, an active ingredient is any component having an effectiveness against a specific skin condition documented through rigorous laboratory testing. The active ingredient provides one or more benefits to the health of the skin tissue to which the dermocosmetic composition is being applied.

Types of active ingredients in a dermocosmetic composition may include, but are not limited to, medicants or active ingredients for specific medical conditions, antioxidants, biologics for cellular benefit, agents for protection against photoaging, analgesics, antibiotics, antimicrobials, pest repellants, skin conditioners, exfoliants, hydration agents, preservatives, antihistamines, cleansing agents, barriers, vitamins, anti-inflammatory agents, small molecules, amino acids, peptides, proteins, ribonucleic acids (RNAs), deoxyribonucleic acids (DNAs), polysaccharides, proteoglycans, glycosaminoglycans, extracellular matrix (ECM) molecules, or combinations thereof.

More specifically, active ingredients in a dermocosmetic composition may include, but are not limited to, alpha-hydroxy acids, beta-hydroxy acid (salicylic acid), vitamin C (citric acid), curcuminoids, hydroquinone, kojic acid, retinol, L-ascorbic acid, hyaluronic acid, copper peptide, alpha-lipoic acid, niacinamide, ceramides, vitamin E, dimethylaminoethanol (DMAE), dexamethasone, aloe, or combinations thereof.

The water, when present in the dermocosmetic composition, serves as the primary solvent to solubilize water-soluble components of the dermocosmetic composition.

The co-solvent, when present in the dermocosmetic composition, aids in solubilizing components with low or no water solubility and may be miscible or immiscible with water. Appropriate co-solvents may include, but are not limited to, an oxygenated solvent, such as for example, an alcohol, a carboxylic acid, an ether, or an ester, an aminated solvent, such as, for example, a primary amine or a secondary amine, a low molecular weight solvent with hydrogen bonding capability, a polar solvent, a non-polar solvent, an ethoxylated low molecular weight solvent, or combinations thereof.

The emulsifier or surfactant, when present in the dermocosmetic composition, aids in compatibilizing the aqueous phase and a non-aqueous phase, when present, to form an emulsion or other similar mixture. The emulsifier promotes the dispersion of the phase in which it does not dissolve well into the phase in which it dissolves well. Appropriate emulsifiers and/or surfactants may include, but are not limited to, ionic surfactants, non-ionic surfactants, cationic surfactants, amphoteric surfactants, amphiphilic surfactants, or combinations thereof.

The bodying agent, when present in the dermocosmetic composition, increases the viscosity of, or thickens, the dermocosmetic composition to give body to the dermocosmetic composition. Appropriate bodying agents may include, but are not limited to, hydrogels, clays, proteins, cellulosics, or combinations thereof.

The filler, when present in the dermocosmetic composition, improves the physical properties of the dermocosmetic composition. Appropriate fillers may include, but are not limited to, titanium dioxide, silica, silicates, iron oxides, carbonates, zinc oxides, or combinations thereof.

Other additives in a dermocosmetic composition may include, but are not limited to, cholesterol, a small chain fatty acid (SCFA), a glycolic acid, a lactic acid, arbutin, vitamin B, vitamin D, estrogen, an antioxidant, lauric acid, amino acids, magnesium oxide (MgO), decanoic acid, retinoic acid, nicotinamide, B-carotene, resveratrol, natural light-active compounds, radical-active compounds, or combinations thereof.

Free glycerol is oily and fugitive as a small molecule, and sebacic acid is solid and requires emulsification and solvency, whereas a preferable glycerol-sebacate component has neither of these disadvantages. In addition, the glycerol-sebacate component having repeating units of (glycerol sebacate) may serve as a sustained release polymer, a vehicle component, a therapeutic delivery matrix, or an elastomeric engineered film capable of mimicking the mechanical properties of full thickness skin. In exemplary embodiments, the glycerol-sebacate component supports cell growth, cell proliferation, cellular health, and molecular health. Specifically, the glycerol-sebacate component may serve as a carrier or vehicle and/or may provide controlled release of one or more of the additives of the dermocosmetic composition.

The glycerol-sebacate component having repeating units of (glycerol sebacate) may be in the form of poly(glycerol sebacate) (PGS), oligomeric (glycerol sebacate) (OGS), PGS flour, and/or PGS microspheres. The PGS may be in resin form or in thermoset form. As used herein, PGS refers to a polymer of (glycerol sebacate) having a weight average molecular weight of greater than 10,000, and OGS refers to an oligomer of (glycerol sebacate) having a weight average molecular weight of 10,000 or less. As used herein, a PGS flour refers to a micronized thermoset PGS filler that has been processed into a powder of a fine powder size, such as, for example, one having an average particle size of less than 1000 micrometers (μm). In addition to molecular weight variations, glycerol-sebacate components may have stochiometric variations as well.

The PGS flour may be formed by any method. In some embodiments, the PGS flour is made by a method disclosed in U.S. Patent Application Publication No. 2017/0246316, published on Aug. 31, 2017, and entitled "Composite Containing Poly(glycerol sebacate) Filler", which is hereby incorporated by reference.

The PGS microspheres may be formed by any method. In some embodiments, the PGS microspheres are made by a method disclosed in U.S. Patent Application Publication No. 2018/0280912, published on Oct. 4, 2018, and entitled "Cured Biodegradable Microparticles and Scaffolds and Methods of Making and Using the Same", which is hereby incorporated by reference.

In some embodiments, the glycerol-sebacate component serves as a base for additives of the dermocosmetic composition. In other embodiments, the dermocosmetic composition may have a conventional or non-glycerol-sebacate base, with the glycerol-sebacate component being included to enhance the base composition, such as, for example, in the form of PGS microspheres.

Depending on the type of dermocosmetic composition, the glycerol-sebacate component may be present in an amount anywhere in the range of 1% to 95%, by weight, of the dermocosmetic composition, such as, for example, 1% to 5%, 5% to 10%, 10% to 20%, 20% to 30%, 30% to 40%, 40% to 50%, at least 50%, 50% to 60%, 60% to 70%, 70% to 80%, 80% to 90%, 90% to 95%, or any value, range, or sub-range therebetween.

The dermocosmetic composition may be used to topically apply an active ingredient to the skin, scalp, or hair. Dermocosmetic compositions may provide bug protection, environmental protection, germ control, sun protection, sunburn relief, photo protection, blue light protection, pollution protection, skin protection, cold stress protection, aging protection, anti-aging, sensory protection, barrier protection, hydration, hair care, skin support, acne treatment, bug-bite treatment, cracked skin treatment, pain relief, infection reduction, accelerated healing, skin allergy care, or combinations thereof.

Any method of forming PGS may be used. In some embodiments, the glycerol-sebacate component is made by a method disclosed in U.S. Pat. No. 9,359,472, issued on Jun. 7, 2016, and entitled "Water-Mediated Preparations of Polymeric Materials", which is hereby incorporated by reference, such as, for example, to provide a component having a low polydispersity index, such as, for example, less than 7.5, less than 7, or less than 6.5.

The glycerol-sebacate component may be free or anchored with one or more additive. In exemplary embodiments, the glycerol-sebacate component is formed under the following conditions, where R in Reaction 1 may be additional glycerol-sebacate repeating units crosslinked to the shown glycerol-sebacate repeating units to form a polymer matrix, another oligomer or polymer grafted to the shown glycerol-sebacate repeating units to form a block co-polymer, or another additive coupled to the shown glycerol-sebacate repeating units:

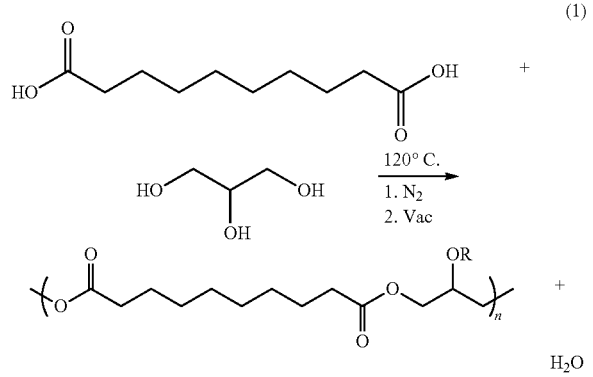
(1)

Additives that are anchorable to the glycerol-sebacate component or matrix at the above R-location may include, but are not limited to, cholesterol, an SCFA, a glycolic acid (such as in a block-PGS), a lactic acid (such as in a block-PGS), ceramides, hyaluronic acid, arbutin, kojic acid (controlled release), vitamin B, vitamin C, vitamin D, estrogen, an antioxidant, lauric acid, amino acids, MgO, salicylic acid, decanoic acid, retinoic acid, nicotinamide, B-carotene, resveratrol, and natural light-active and radical-active compounds. Any number of hydroxyl-bearing and/or carboxyl-bearing groups may be polymerized into the glycerol-sebacate component by a water-mediated method or other methods of PGS processing.

In some embodiments, the glycerol-sebacate component is co-polymerized, is in a PGS-block copolymer, or is co-blended. Certain benefits that PGS has in the regenerative medicine and tissue engineering technologies are preferably conferred to dermocosmetic compositions for skin therapy, healing, regeneration, conditioning, and maintenance of integument health.

Glycerol (glyceryl) esters formed by the glycerol-sebacate component may include, but are not limited to, a glycerol triglyceride of SCFA, a glyceryl acrylate/acrylic acid, a glyceryl arachidonate, a glycerol behenate, a glyceryl caprylate, a glyceryl dibehenate, a glyceryl isostearate, a glyceryl laurate, a glyceryl linoleate, a glyceryl isostearate, a glyceryl monostearate, a glycerol oleate, a glycerol para amino benzoic acid (PABA), a glyceryl polymethylmethacrylate, a glycerol ricinolate, a glycerol stearate, a glyceryl stearate citrate, a glyceryl stearate lipophilic, a glyceryl tribehenate, a glyceryl triisostearate, a glyceryl trioctenoate, or combinations thereof. The glycerol-sebacate component is preferably not a small molecule but rather a bis-glycerol triglyceride of a diacid.

In exemplary embodiments, the polymerization of the sebacic di(carboxylic)acid creates a matrix structure. SCFAs provide antimicrobial activity. These monoacids may be co-polymerized as well with sebacic acid (diacid) into the matrix, providing mixed-matrix chemistries.

The unique ability to control the release of both free and anchored metabolites as well as grafting components of skin care such as amino acids, vitamins, and minerals combined with the compatibility with biopolymers such as collagen and alginate polymers add to the value of glycerol-sebacate components in dermocosmetic products.

In exemplary embodiments, the dermocosmetic composition further includes one or more additives beneficial to skin care and therapy anchored or blended into the matrix. The one or more additives may be present in any appropriate amount. Appropriate amounts of additives may include, but are not limited to, anywhere in the range of 0.1% to 90%, by weight, of the dermocosmetic composition, such as, for example, 0.1% to 1%, 1% to 5%, 5% to 10%, 10% to 20%, 20% to 30%, 30% to 40%, 40% to 50%, 50% to 60%, 60% to 70%, 70% to 80%, 80% to 90%, or any value, range, or sub-range therebetween.

The glycerol-sebacate component delivers the components of the polymer and its modifications, including additives that address one or more dermocosmetic issues, to the skin in either a controlled release or compatibility fashion. In exemplary embodiments, the glycerol-sebacate component efficiently delivers nutrient and/or medicinal components in a manner that does not require over-formulating or extreme use of additives for stability and application to achieve results and benefits from certain properties of the glycerol-sebacate component.

In exemplary embodiments, the glycerol-sebacate component selectively delivers components and takes advantage of the chemical and biomechanical properties of the glycerol-sebacate component in skin conditioning as well as films and coatings for protection. In polymer form as a viscoelastic solid, the glycerol-sebacate component is a bioresorbable elastomer. The dermocosmetic product may provide healing, regeneration, and/or maintenance to the skin.

PGS has a number of advantageous properties for use in dermocosmetic compositions. PGS is transparent to ultraviolet (UV) light, allowing for a vehicle that does not compete with UV absorbers. Infrared (IR) and microwave (MW) absorption by PGS may be beneficial to skin exposed to low-frequency electromagnetic (EM) radiation. The ultraviolet-visible light (UV-Vis) transparency of PGS supports "blue-light", IR, and MW protection. PGS tends to have lipophilic properties but may be modified stoichiometrically to be hydrophilic. PGS may serve as a crossover component between tissue engineering and dermocosmetic additives where trophic agents and biologic formulation finds favor. PGS may serve as a vehicle or compounding agent for vitamins A, D, E, and K because of its lipid-like character. This PGS lipid-like character may aid in delivery of additive to dermal layers and help protect against cold stress damage. PGS provides a polymeric amphoteric controlled compatibility for release and/or as a formulating base that can hold charged species of additives.

The presence of glycerol in the glycerol-sebacate component may provide certain advantages in a dermocosmetic composition. The polymeric/oligomeric form of glycerol in a glycerol-sebacate component may drastically reduce or eliminate an undesirable "oily" feel and the avoidance of use by people with oily skin to benefit from the anti-inflammatory and barrier recovery features of glycerol. The polymeric/oligomeric form of glycerol may aid in the UV protection of skin, where glycerol-absorber-energy transfer agent-free radical terminator delivery to the skin chemistry is aided. The polymeric/oligomeric form of glycerol may help stabilize components from fugitive action.

In some embodiments, the glycerol-sebacate component provides a "polymeric" or "oligomeric" form of any skin care additive having the appropriate functionality to react into the glycerol-sebacate matrix or compound into the formulation for different action in use in addition to the tissue benefits of the glycerol-sebacate component alone.

The glycerol-sebacate component offers a multi-featured option in formulation. The polymeric or oligomeric form of glycerol and sebacic acid provides a vehicle-carrier platform approach, a matrix-entrapped stabilization from fugitive action, and the functional benefit of controlled release of ingredients and delivery or exposure in dermocosmetic formulations in immediate and temporal fashion. The glycerol-sebacate component may be considered as both a compounding vehicle as well as a platform matrix to react in, anchor, or entrap target additives for care.

As a surface-eroding system, the biodegradable erosion base of the dermocosmetic formulation is at the glycerol-sebacate component/epidermis interface. This allows the bulk vehicle to also provide bulk barrier "film" or "structured" features to the applied product based on solids, molecular weight, and hydrophobic/hydrophilic balance.

The glycerol-sebacate component, in an oligomeric or polymeric form of resin or biodegradable elastomer, can deliver ingredients through diffusion and/or surface erosion.

The glycerol-sebacate component, in an oligomeric or polymeric form of resin or biodegradable elastomer, can deliver ingredients in a spatiotemporal manner.

PGS is a bis-glycerol triglyceride of a diacid polymeric form of a lipid triglyceride-like structure and may be designed to substitute for animal-based triglycerides, thereby eliminating allergy, religious, or ethnic issues, while providing a base formulating platform for creams, ointments, and salves. The glycerol-sebacate component structure may be designed to be an emollient, occlusive, and/or moisturizer.

A PGS platform may be a "carrier" for hydroxyl- or carboxyl-bearing ingredients. Using a glycerol-sebacate component as a controlled release vehicle or additive allows the formulator to modulate the temporal needs of skin care and provide metabolites as part of the functionality and feature of biodegradability. Preferred embodiments provide a consumer-friendly ability to apply a dermocosmetic product containing a glycerol-sebacate component as a cream, ointment, salve, or liquid, which may be diluted in aqueous media to spray, coat, sponge, bathe, or hand-deliver the dermocosmetic product. The glycerol-sebacate component may be designed to be an effective biodegradable occlusive to optimize moisture barrier and hydration balance. The glycerol-sebacate component may be designed to be used as a polymeric emulsifier/surfactant for oils and fatty acids. The glycerol-sebacate component may be substituted for petrolatum, thereby minimizing photoaging by feeding cells as well as being biodegradable and occlusive.

In exemplary embodiments, a glycerol-sebacate component provides to dermocosmetic compositions all the previously-described benefits to regenerative medicine and tissue engineering with a focus on regeneration and rejuvenation.

A glycerol-sebacate component with application of molecular weight control to the product design is capable of simplifying and stabilizing complex formulations and preventing component separation by free energy. For instance, addition of essential amino acids into an aqueous skin conditioner requires the hydrophilic/lipophilic balance (HLB) for the nutrient amino acid to remain uniformly distributed in the composition throughout storage and shelf-life. Having components bound or anchored to the glycerol-sebacate component not only insures a uniform application at the time of use but prevents the essential amino acid from "falling out" of the distribution, dispersion, emulsion, or solution. Furthermore, a polymeric or oligomeric version of glycerol and sebacic acid is capable of optimizing the uniform distribution of glycerol as a humectant and sebacic acid as a pH balancer. Likewise, any component bound to the glycerol-sebacate component temporally and uniformly provides the appropriate delivery as determined by the formulation and application conditions.

In exemplary embodiments, the glycerol-sebacate component provides one or more of the following attributes to the dermocosmetic composition: endogenous regeneration, bioresorbability, custom controlled degradation, zero-order release of additives, degradation to metabolites through natural hydrolytic processes, immunomodulation, antimicrobial activity, elastomeric film conformation, hemocompatibility/non-thrombogenicity, formation of breakdown products metabolically favorable to cell proliferation, pro healing action, mechanical tissue compliance, non-irritation, non-cytotoxicity, biocompatibility, non-toxicity, effectiveness in a targeted area for at least 5 days, biological degradability, non-interference with normal healing processes, non-interference with immunological functions, applicability in certain settings, including, but not limited to, bleeding, infections, and anastomotic surgery, easy application/conformation, compatibility with certain biopolymers, including, but not limited to, collagen, alginates, and ECM materials, such as, for example, proteins, glycoproteins, lipids, and blood products, and processability to create mechanically similar biodegradable skin-film protection for chronic skin conditions.

In some embodiments, the presence of the glycerol-sebacate component upregulates or downregulates one or more genes to the benefit of promoting healthy skin at or near the application site of the dermocosmetic composition including the glycerol-sebacate component. Such genes may include, but are not limited to, Collagen Type IV Alpha 2 ($COL_4A_2$), which strengthens the ECM, Tissue Inhibitor of Matrix Metalloproteinases 1 ($TIMP_1$), which degrades matrix metalloproteinase-1 (MMP1), Superoxide Dismutase 2, mitochondrial antioxidant manganese superoxide dismutase (MnSOD) ($SOD_2$), which protects against oxidative stress, and Transglutaminase 1 ($TGM_1$), which is necessary for formation of the cornified cell envelope.

Blue-light skin damage results from prolonged exposure to blue light, with damage-causing emissions peaking at a wavelength of about 440 nm. Certain artificial lighting, flat screen monitors, and computer devices all emit light at this wavelength, causing chronic damage to the skin. In some embodiments, a dermocosmetic formulation includes a glycerol-sebacate component, beta-carotene, vitamin E, niacin, nicotinamide, salicylic acid, lignin extract, tartrazine, curcumin, and/or turmeric and provides blue light protection. The glycerol-sebacate component may be free or anchored with one or more additive.

Cold stress occurs when skin is exposed to cold temperatures, which locally reduces the temperature of the skin below normal body temperature. During cold stress, major lipids in the skin, including fatty acids, ceramides, and cholesterol, are decreased, thus making it more difficult for epithelial cells to proliferate, thereby affecting the barrier structure of the skin and its protective role. Cold stress generates pro-inflammatory mediators, leading to further tissue damage. In addition, when temperatures decline below normal body temperature, capillary physiology changes, and the penetration resulting from endothelial cell activity is reduced. PGS is capable of endothelial support, and as a polymeric lipid, the glycerol-sebacate component may mitigate cold stress in skin and serve to replenish skin integrity via breakdown products of the glycerol-sebacate component. In some embodiments, a dermocosmetic formulation includes a glycerol-sebacate component, olive oil, vitamin E, thiamin, riboflavin, niacin, pyridoxine, cobalamin, folic acid, pantothenic acid, biotin, nicotinamide, and/or beeswax and provides cold stress protection. The glycerol-sebacate component may be free or anchored with one or more additive.

Methods of application have been described herein for dermocosmetic use but a glycerol-sebacate component may similarly be used as a foundation or base for OTC cosmetics, other skin care products, and/or wound care products. In some embodiments, the dermocosmetic composition supports a wound care treatment, treats a post-chronic condition after the wound care treatment, or maintains healed skin after the wound care treatment.

Dermal healing and scar formation are greatly impacted by the natural lines of tension in the skin, also known as Langer's lines. All humans have similar Langer's line patterns, but slight differences exist between individuals based on their underlying bone structure and anatomy. Langer's lines follow the collagen fiber orientation in the dermis, and they also run parallel to the orientation of underlying muscle fibers. During surgery, surgeons prefer to create incisions along these lines, if possible, since incisions made parallel to Langer's lines may heal better and produce less scarring than incisions cut across Langer's lines. Perpendicular incisions tend to pucker and remain more obvious, and for injuries, this can have an impact on the presentation of the wound.

In some embodiments, a glycerol-sebacate component in the form of PGS, PGS-alginate, or blends of PGS with other polymers is fabricated into a dermal patch for scar reduction. The patch is composed of PGS-based sheets, films, and/or fibers, and utilizes the elastomeric properties of PGS to apply directed, controlled compression to the dermal wound. Similar to the z-plasty technique used in cosmetic and orthopedic surgery and commercial elastomer compressive gels, a patch oriented in the appropriate direction applies compressive forces to reduce tension during wound healing, reducing and relieving scar formation. Specifically, a cause of scar formation is the contracture by fibroblasts on produced collagen I fibers that the cells have deposited as initial granulation tissue. During fibroblast contraction, the normally disorganized collagen fibers become aligned under the contraction force, leading to the appearance of a scar. Fibroblast hypertrophy also occurs through mechano-transduction from the taut collagen fibers, leading to overproduction of collagen type I, which presents as a bulky scar without hair follicles. Normal wound healing, where scarring does not occur, results in a randomized collagen fiber alignment, which is preferential to achieve normal skin function and appropriate strength. A compressive dermal patch applied to a wound offsets fibroblast contracture, reduces collagen fiber alignment, and prevents excessive hypertrophy of collagen I, all of which alleviate scar formation.

In some embodiments, the dermal patch including a glycerol-sebacate component may be uniform or may have directionality, applying compression in certain axes and tension in other axes. The directionality of the dermal patch depends on the site of application with the knowledge of Langer's lines topography.

In some embodiments, the patch for scar reduction including the glycerol-sebacate component is applied to the wound of a patient by additive manufacturing, and preferably more specifically three-dimensional (3D) printing, on-demand based on the geometry and the topography of the patient's wound. The additively-manufactured patient-specific products may be dispensed in a pharmacy or in a hospital. In some embodiments, prior to additive manufacturing of the patch, the topology of the skin surface is identified, and Langer's lines are mapped onto the skin surface in the area of the wound by 3D scanning. The boundaries of the wound are identified by image segmentation. The wound is then placed in the context of the Langer's lines, and a patch design with fiber geometries that reduce tension is generated, prior to additive manufacturing of the patch onto the wound based on the patch design.

Aside from wound healing, during the aging process, wrinkles in the skin form along these Langer's lines, and some elastomeric films have been commercialized to smooth out the skin by applying tension that reduces the visibility of deep lines. In some embodiments, a sheet or patch including a glycerol-sebacate component may be used as a topical product, applied daily as a temporary cosmetic enhancement to smooth out the appearance of wrinkles. The sheet or patch may contain spatial, temporal, and/or formulational elements that are patient-specific, using 3D scanning, imaging, or mapping of the individual. 3D printing may be used to fabricate such custom designs.

In some embodiments, a sheet or patch including a glycerol-sebacate component may be used as a facial mask, such as, for example, for hydration, moisturizing, healing, soothing, and/or delivery of active and/or inactive ingredients. The sheet or patch may contain spatial, temporal, and/or formulational elements that are patient-specific using 3D scanning, imaging, or mapping of the individual. 3D printing, inkjet deposition, and/or laser cutting may be used to fabricate such custom designs.

In some embodiments, a glycerol-sebacate component may be used in combination with or fabricated into microneedles, such as, for example, to assist in transdermal delivery of active and/or inactive ingredients across the keratinocyte barrier, and/or to assist in transdermal delivery of the glycerol-sebacate itself. This may be especially useful for macromolecules, proteins, and other agents that cannot easily permeate into skin, cannot survive oral ingestion through the gastrointestinal tract, and/or in situations where topical delivery to the site is advantageous over oral administration. Microneedles may be composed of, coated with, or used alongside a gel or sheet of glycerol-sebacate. Microneedles may contain spatial, temporal, and formulational elements that are patient-specific, using 3D scanning, imaging, or mapping of the individual. 3D printing, inkjet deposition, and/or lithography may be used to fabricate such custom designs.

In some embodiments, a dermocosmetic formulation includes a glycerol-sebacate component, vitamin E, thiamin, riboflavin, niacin, pyridoxine, cobalamin, folic acid, pantothenic acid, biotin, and/or salicylic acid and provides anti-aging. The glycerol-sebacate component may be free or anchored with one or more additive.

EXAMPLES

The invention is further described in the context of the following examples which are presented by way of illustration, not of limitation.

Example 1

Human Schwann cells were exposed to varying amounts of PGS in tissue culture for 28 days. The cytocompatibility was tested on a neat extract including PGS (100%) and dilutions to 50%, 10%, and 1% extracts. The relative cytocompatibility of each sample was measured at days 7, 14, 21, and 28. FIG. 1 shows that the degradation products of PGS also increase cell proliferation in human Schwann cells. The cytocompatibility was normalized to tissue culture polystyrene (TCPS) in the absence of PGS. The proliferation of human Schwann cells was found not to be negatively impacted by exposure to the degradation products of PGS over the 28-day period.

Example 2

Figure 2:
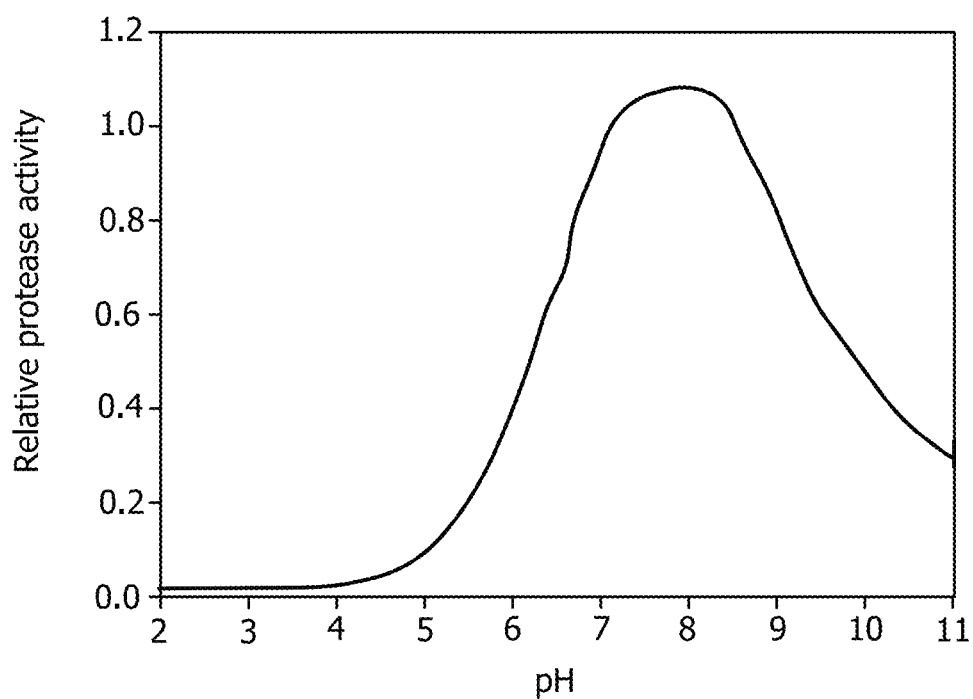
FIG. 2 shows protease activity as a function of pH during healing.

The curve in FIG. 2 shows the relative protease activity at a wound site, which varies drastically with the pH at the wound site. FIG. 2 illustrates the importance of maintaining a low pH during the early phases of healing to minimize protease activity, which can be "non-healing" if left uncontrolled at a neutral or basic pH. The presence of sebacic acid at the wound site, as a consequence of degradation of the glycerol-sebacate component, lowers the pH, which may help modulate the wound site and/or skin pH for an ideal healing environment.

Example 3

Figure 3:
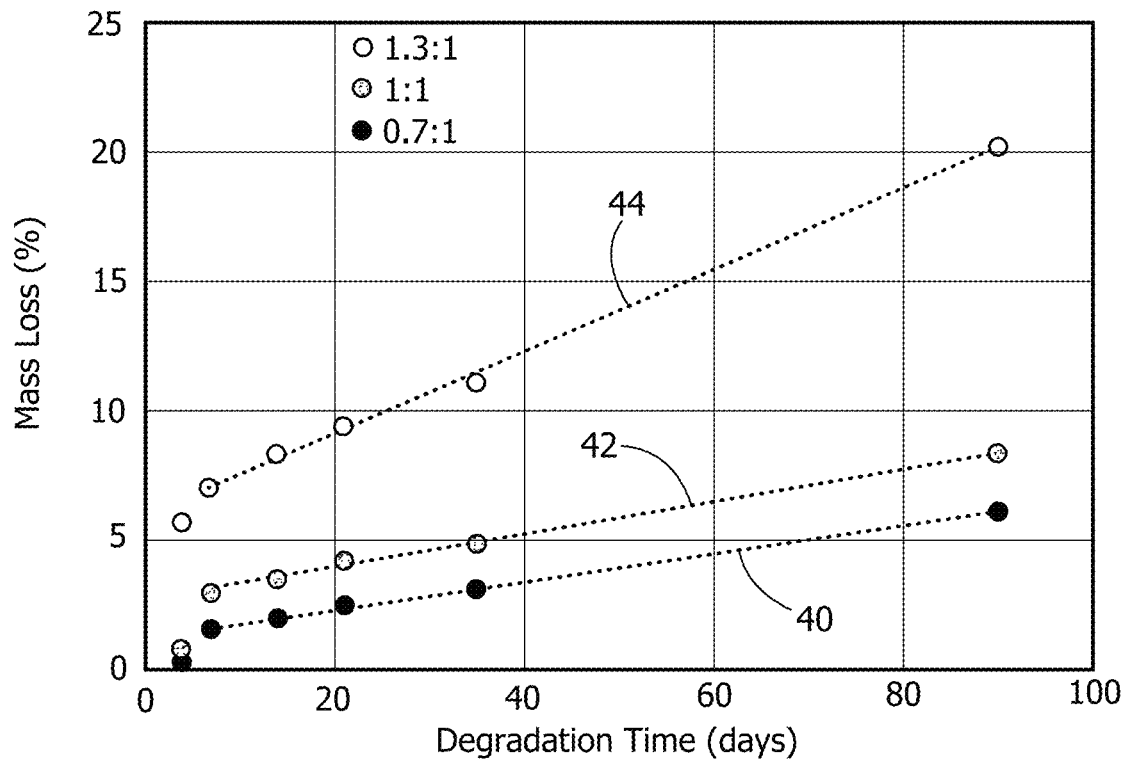
FIG. 3 shows the effect of the glycerol:sebacic acid ratio on PGS degradation rate.

PGS resin samples were polymerized from three different glycerol:sebacic acid mole ratios, 0.7:1, 1:1, and 1.3:1, under otherwise identical water-mediated conditions. Thermoset versions of the PGS samples were placed in water, and the degradation of the samples was measured as a percentage of mass loss over a 90-day period. FIG. 3 shows that while all three samples degraded linearly from day 7 up to day 90, indicating surface degradation, the degradation rate increased with increasing glycerol:sebacic acid mole ratio, as seen by comparing the 0.7:1 ratio line 40 to the 1:1 ratio line 42 and the 1:1.3 ratio line 44.

Example 4

Figure 4:
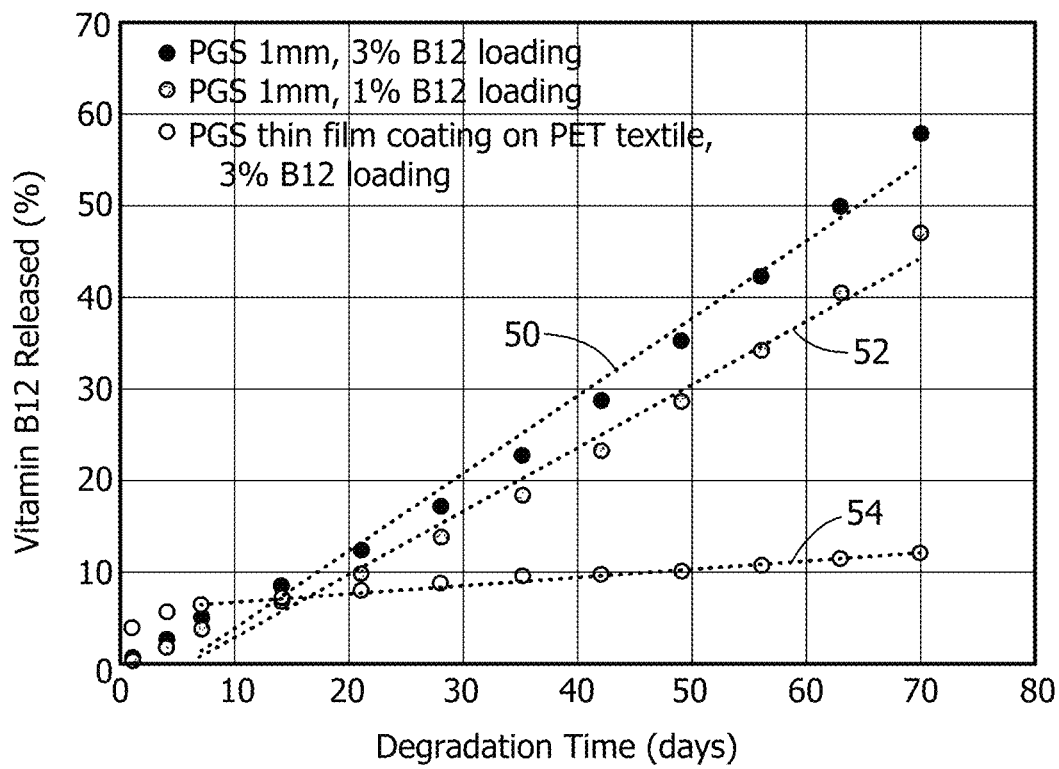
FIG. 4 shows zero-order controlled release of cobalamin from PGS.

Three different samples of cobalamin (vitamin B12)-loaded PGS were prepared and tested for release of the vitamin B12 in an aqueous environment. In one sample, PGS resin was loaded with 1% vitamin B12, by weight, and cured for 48 hours to form a 1 mm PGS thermoset film. In a second sample, PGS resin was loaded with 3% vitamin B12, by weight, and cured for 48 hours to form a 1 mm PGS thermoset film. In a third sample, PGS resin was loaded with 3% vitamin B12, by weight, and applied as a thin film to a textile made of polyethylene terephthalate (PET). FIG. 4 shows the measured zero-order controlled release of vitamin B12 from PGS. The 3% loading 50 provided a slightly higher relative release rate than the 1% loading 52. The coating 54 released vitamin B12 at a significantly lower relative rate than either of the other two samples. Zero-order controlled release from PGS has also been observed for vitamin E and curcumin.

Example 5

Figure 5:
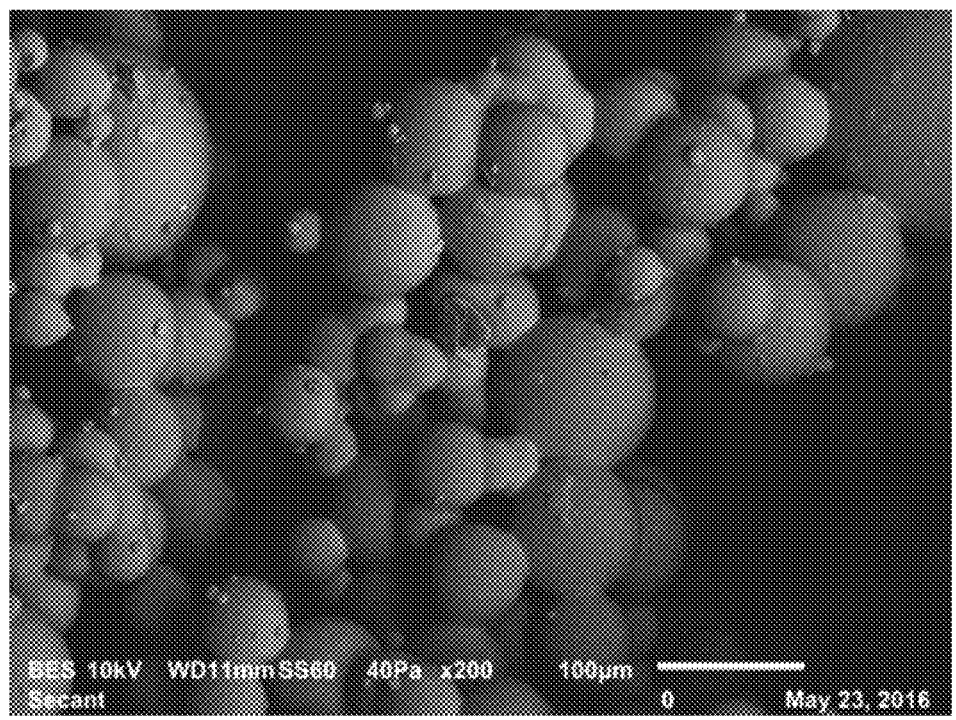
FIG. 5 shows PGS microspheres for incorporation into dermocosmetic compositions in an embodiment of the present disclosure.

FIG. 5 shows PGS formed into microspheres for incorporation into dermocosmetic compositions. The PGS microspheres may be unloaded or loaded with one or more additives. The particle size may be tuned, for example, by adjusting the intensity of shear mixing by adjusting the number of revolutions per minute (RPM), the impeller size and/or shape, and/or the size and shape of the reaction vessel, by adjusting the continuous phase:dispersed phase ratio, by adjusting the viscosity of the continuous phase, by adjusting the viscosity of the dispersed phase, and/or by the absence or presence and amount of emulsifiers and/or stabilizers.

Example 6

Figure 6:
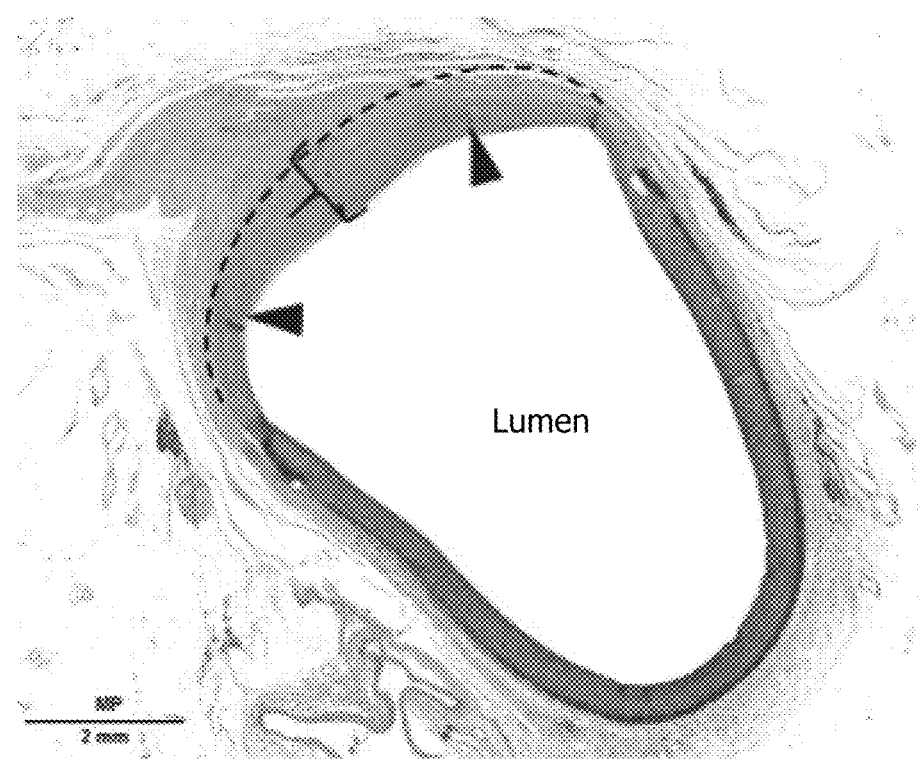
FIG. 6 shows a stained cross section of a neo-vessel repaired with a PGS-coated patch.

A polyglycolic acid (PGA) cardiovascular patch was coated with PGS and implanted into a defect made in the carotid artery of a sheep. The carotid defect and surrounding tissue were harvested at three months and processed for histopathological analysis. FIG. 6 shows a representative cross-section through the distal portion of the PGS-coated PGA cardiovascular patch. The area of the patch placement with the presence of an endothelial layer and the absence of graft material in a repaired area is indicated by a dashed line. Uniform reconstruction of the vascular wall by a fibromuscular tissue is indicated by a bracket and arrowheads. The image indicates an endothelialized lumen with no evidence of vascular occlusion, such as, for example, via neointimal growth or thrombosis. No evidence of adverse pathology, such as, for example, exuberant inflammation and/or necrosis, was observed. This result suggests that PGS encourages vascular reconstruction and endothelial proliferation in neo-vessels, as may be needed in dermal capillary beds.

Example 7

Figures 7A, 7B, 7C:
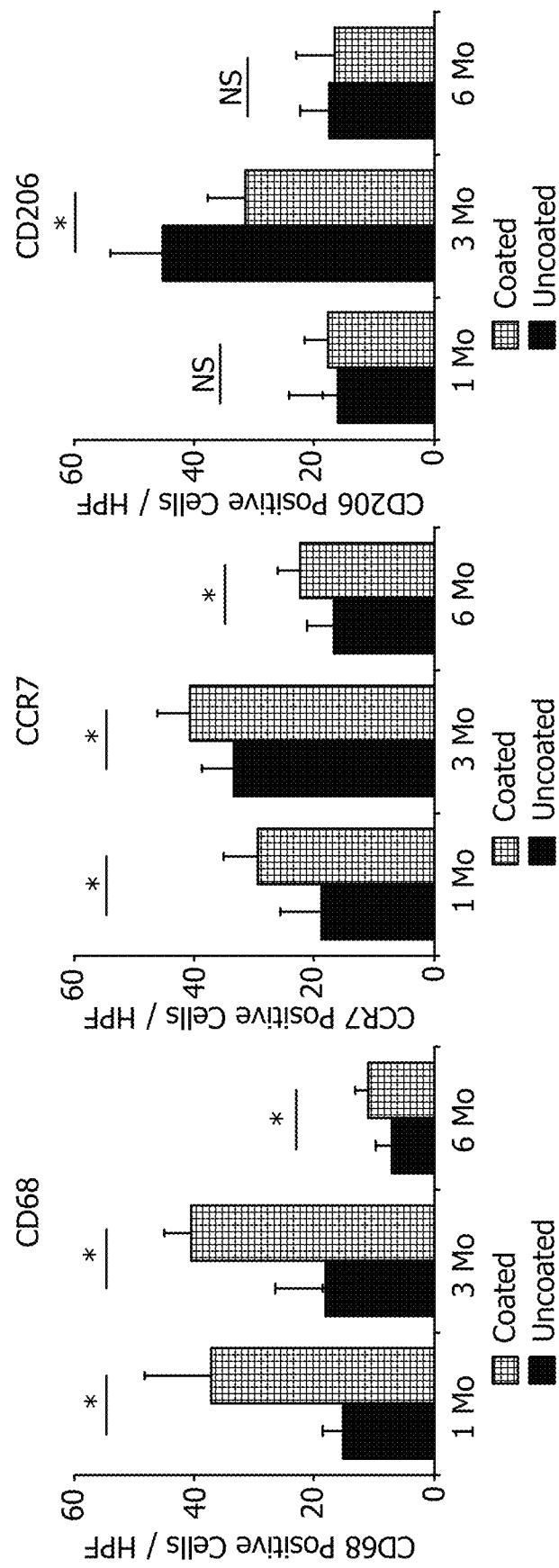
FIG. 7A shows the total macrophage expression (CD68) for PGS-coated and non-coated cardiovascular grafts at 1, 3, and 6 months post-implant.
FIG. 7B shows the M1 macrophage expression (CCR7) for PGS-coated and non-coated cardiovascular grafts at 1, 3, and 6 months post-implant.
FIG. 7C shows the M2 macrophage expression (CD206) for PGS-coated and non-coated cardiovascular grafts at 1, 3, and 6 months post-implant.

PGS-coated and uncoated cardiovascular grafts were implanted and then tested for macrophage expression post-implant. The grafts were implanted as infrarenal abdominal aorta inter-positional grafts in a rat for periods of one, three, and six months. FIG. 7A shows the total macrophage expression (CD68) on PGS-coated (solid bar) and non-coated (checkered bar) cardiovascular grafts at one, three, and six months post-implant. FIG. 7B shows the M1 macrophage expression (CCR7) on PGS-coated and non-coated cardiovascular grafts at one, three, and six months post-implant. FIG. 7C shows the M2 macrophage expression (CD206) on PGS-coated and non-coated cardiovascular grafts at one, three, and six months post-implant. Total macrophage expression is lower and M2 expression is elevated at 3 months in the PGS-coated grafts relative to the uncoated grafts.

Example 8

Figure 8:
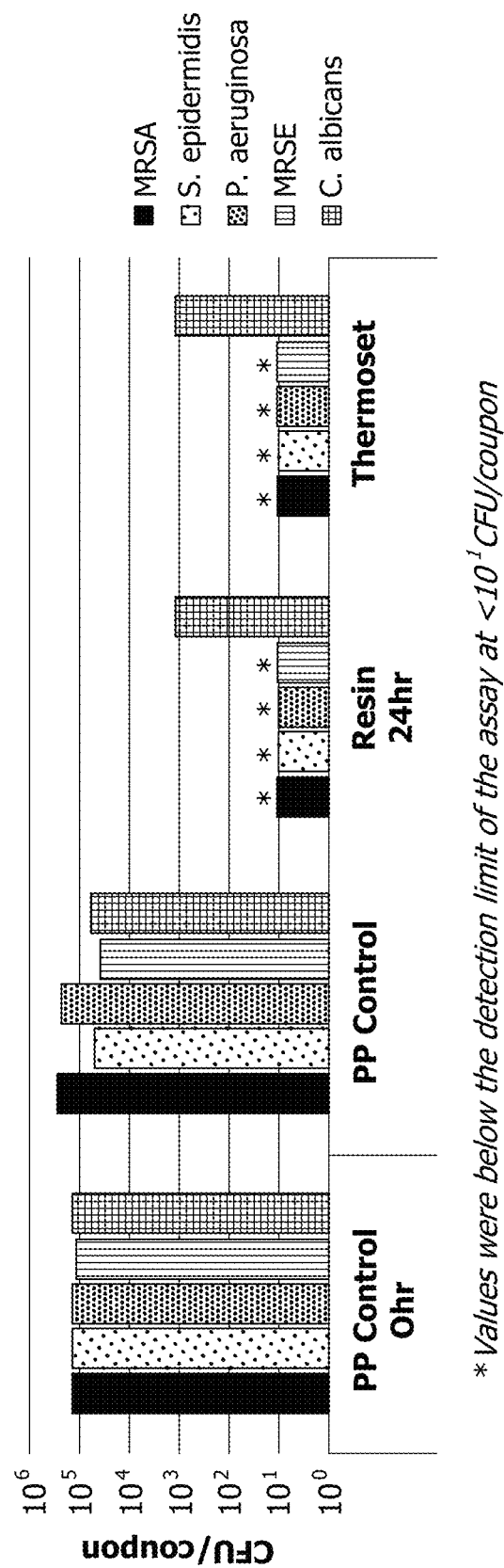
FIG. 8 shows the antimicrobial activity of PGS resin and thermoset against five common pathogens relative to a polypropylene (PP) control.

The antimicrobial activity of PGS in both resin and thermoset forms was tested against five common pathogens, methicillin-resistant *Staphylococcus aureus* (MRSA), *Staphylococcus epidermidis, Pseudomonas aeruginosa*, methicillin-resistant *Staphylococcus epidermidis* (MRSE), and *Candida albicans* using the JIS Z2801 method (ISO 22196). FIG. 8 shows measured microbial colony forming unit (CFU) counts after 24 hours relative to a polypropylene (PP) control. PGS in both resin and thermoset forms showed strong antimicrobial activity against all five pathogens.

Example 9

Figure 9:
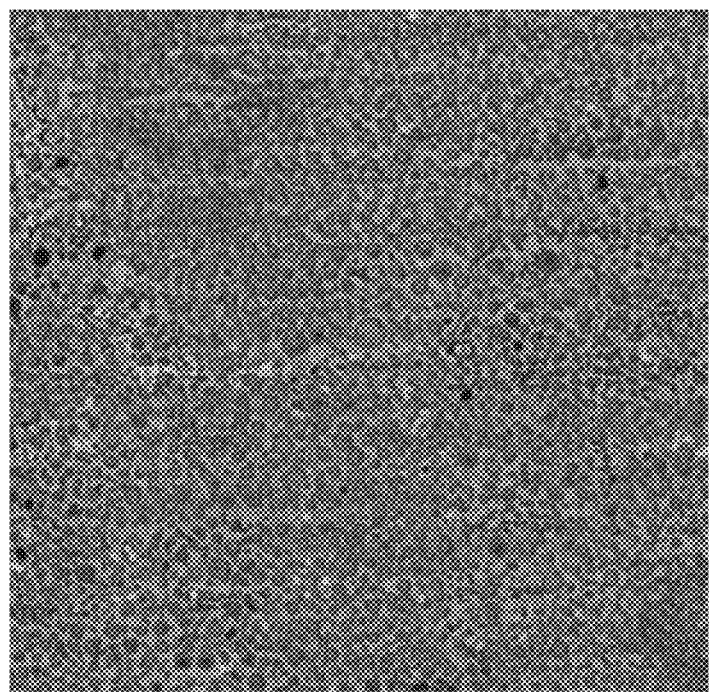
FIG. 9 shows the phase separation distribution of PGS in polyisobutylene (PIB).

FIG. 9 shows the phase separation distribution of PGS resin and polyisobutylene (PIB) resin in a 50:50 w/w mixture, indicating a delivery method or formulation option for skin care and use. The image in FIG. 9 was obtained by a laser-directed infrared (LDIR) microscope (Agilent Technologies, Santa Clara, Calif.). The lighter areas in FIG. 9 represent the PGS, whereas the darker areas represent the PIB.

Example 10

Figure 10:
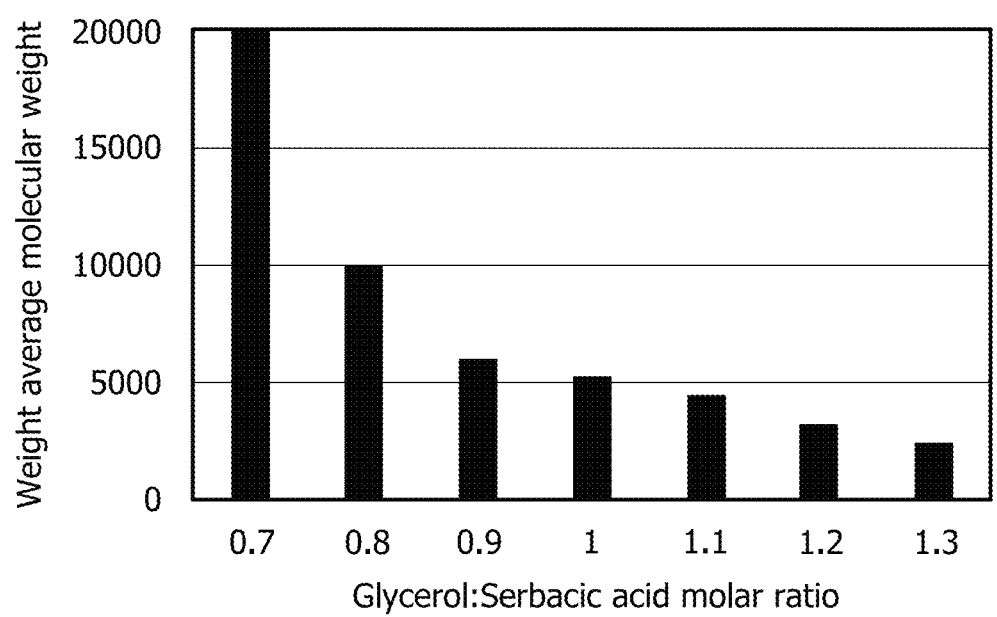
FIG. 10 shows weight average molecular weights of glycerol-sebacate components based on gel permeation chromatography (GPC) data for PGS with seven different glycerol:sebacic acid ratios.

Glycerol-sebacate components were formed with ratios of glycerol to sebacate of 0.7:1, 0.8:1.0, 0.9:1.0, 1.0:1.0, 1.1:1.0, 1.2:1.0, and 1.3:1.0. The resulting compositions were tested for molecular weight by GPC, for hydrophilicity/hydrophobicity, and for viscosity. FIG. 10 shows that stoichiometric variation of the polymerization process affords the ability to control the molecular weight of the resulting PGS polymer. Stoichiometric variations may also be used to vary the properties of the glycerol-sebacate component from hydrophilic (1.3:1.0 ratio) to neutral (1.0:1.0 ratio) to hydrophobic (0.7:1.0 ratio) and from high viscosity (0.7:1.0 ratio) to low viscosity (1.3:1.0 ratio).

Example 11

Figure 11:
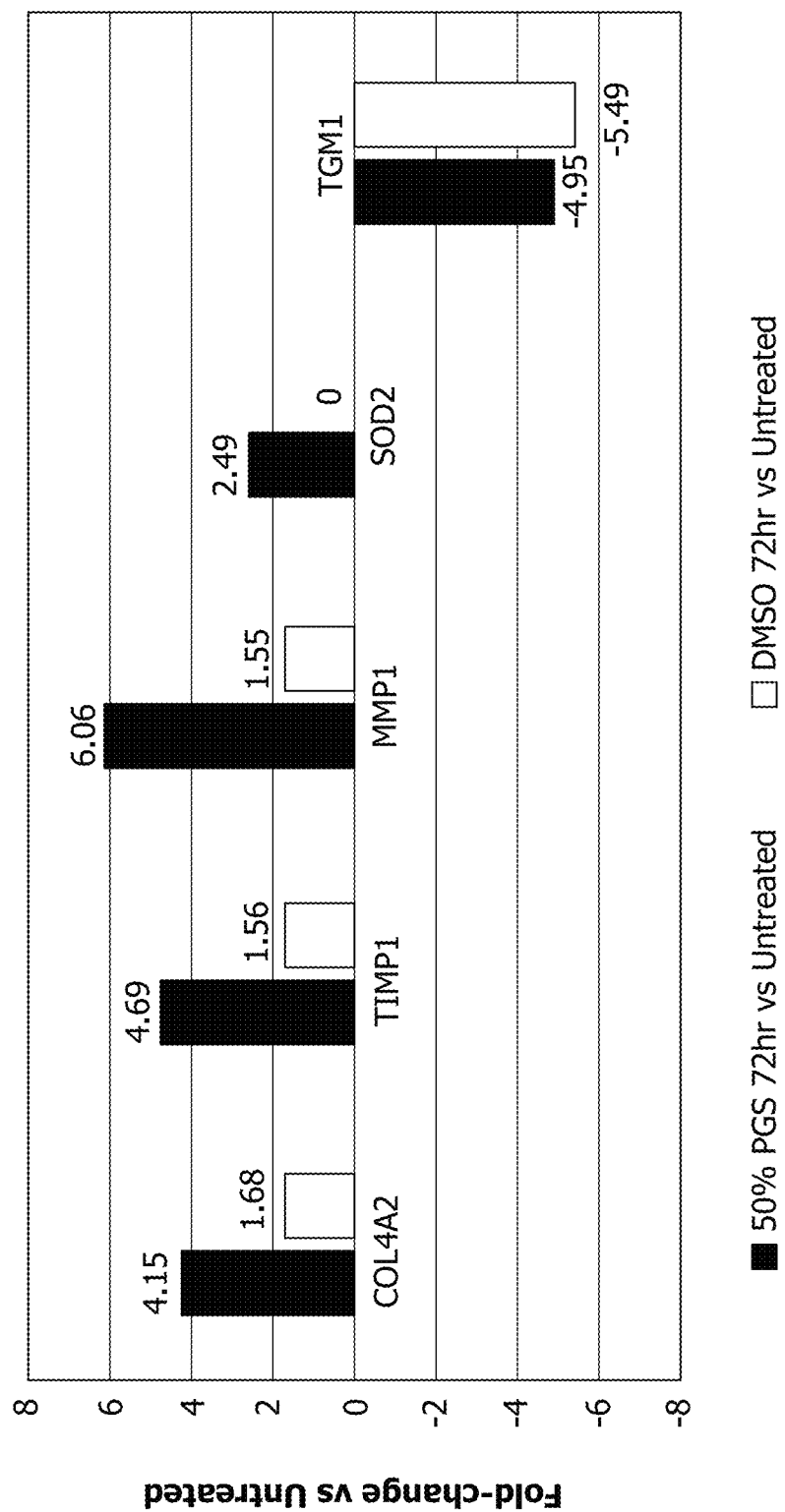
FIG. 11 shows the effect of the presence of a glycerol-sebacate component on gene expression of five genes relative to a control composition.

A genetic study was conducted to understand how gene expression in the skin is influenced by the presence of PGS. The study was performed using a full-thickness in vitro skin culture model containing epidermal and dermal cell layers (EFT-400, MatTek Corp., Ashland, Mass.). Gene expression was assessed in the full-thickness tissues following either 24-hour or 72-hour exposure to PGS. The following treatment groups were included in the study (N=4): 1) PGS (10% w/w in DMSO), 2) PGS (50% w/w in DMSO), 3) vehicle control [DMSO], and 4) untreated control. Gene expression was analyzed using a Standard Skin Panel (Genemarkers, LLC, Kalamazoo, Mich.), a qPCR-based gene expression panel that contains 107 target genes and 5 endogenous control genes. FIG. 11 shows that the gene expressions for $COL_4A_2$, $TIMP_1$, MMP1, $SOD_2$, and $TGM_1$ were all affected by use of PGS on a full-thickness in vitro skin culture model containing epidermal and dermal cell layers.

While the invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A method of skin care comprising:
    applying a dermocosmetic composition to a skin surface, the dermocosmetic composition comprising:
    at least one additive comprising at least one active ingredient; and
    at least one glycerol-sebacate component having repeating units of (glycerol sebacate);
    wherein the at least one additive is covalently attached to the glycerol-sebacate component; and
    wherein the applying comprises applying the dermocosmetic composition as a dermal patch to the skin surface based on Langer's lines.

2. The method of claim 1, wherein the at least one additive is selected from the group consisting of cholesterol, a small chain fatty acid, a glycolic acid, a lactic acid, arbutin, vitamin B, vitamin D, estrogen, an antioxidant, lauric acid, an amino acid, magnesium oxide, decanoic acid, retinoic acid, nicotinamide, B-carotene, resveratrol, a natural light-active compound, a radical-active compound, and combinations thereof.

3. The method of claim 1, wherein the at least one active ingredient is selected from the group consisting of an alpha-hydroxy acid, a beta-hydroxy acid, salicylic acid, citric acid, a curcuminoid, hydroquinone, kojic acid, retinol, L-ascorbic acid, hyaluronic acid, copper peptide, alpha-lipoic acid, niacinamide, a ceramide, a peptide, vitamin E, dimethylaminoethanol, and combinations thereof.

4. The method of claim 1, wherein the at least one glycerol-sebacate component is selected from the group consisting of poly(glycerol sebacate), oligomeric (glycerol sebacate), and thermoset poly(glycerol sebacate) flour.

5. The method of claim 1, wherein the dermocosmetic composition further comprises water, a co-solvent, and a component selected from the group consisting of an emulsifier, a surfactant, a bodying agent, and combinations thereof.

6. The method of claim 1, wherein the at least one glycerol-sebacate component is applied for the purpose of altering an expression of at least one gene in skin after application of the dermocosmetic composition to the skin surface.

7. A method of skin care comprising:
- providing a dermocosmetic composition comprising at least one glycerol-sebacate component having repeating units of (glycerol sebacate), the dermocosmetic composition having an effective amount of the at least one glycerol-sebacate component to alter an expression of at least one gene in skin after application of the dermocosmetic composition to the skin surface; and
- applying the dermocosmetic composition to a surface of the skin such that the expression of the at least one gene in the skin is altered by the at least one glycerol-sebacate component;
- wherein the dermocosmetic composition further comprises at least one additive comprising at least one active ingredient;
- wherein the at least one additive is covalently attached to the glycerol-sebacate component; and
- wherein the applying comprises applying the dermocosmetic composition as a dermal patch to the skin surface based on Langer's lines.

* * * * *